United States Patent [19]

Forgione et al.

[11] Patent Number: 5,089,617
[45] Date of Patent: Feb. 18, 1992

[54] BETA-HYDROXYALKYLCARBAMYL-METHYLATED AMINOTRIAZINES

[75] Inventors: Peter S. Forgione; Balwant Singh, both of Stamford, Conn.

[73] Assignee: American Cyanamid Company, Stamford, Conn.

[21] Appl. No.: 120,570

[22] Filed: Nov. 13, 1987

Related U.S. Application Data

[62] Division of Ser. No. 864,626, May 16, 1986, Pat. No. 4,708,984.

[51] Int. Cl.$^5$ .................. C07D 251/18; C07D 251/70
[52] U.S. Cl. ..................................... 544/196; 544/205
[58] Field of Search ............................. 544/196, 206

[56] References Cited

PUBLICATIONS

Forgione et al., Chemical Abstracts, vol. 109, entry 75378q. (1987).
Forgione et al., Chemical Abstracts, vol. 109 entry 56694r (1987).

*Primary Examiner*—John M. Ford
*Attorney, Agent, or Firm*—Roger S. Benjamin

[57] ABSTRACT

Novel beta-hydroxyalkylcarbamylmethyl aminotriazines function in self-condensation and as cross-linkers for amino resins and also compounds containing active hydrogen groups. The compositions cure to coatings with excellent properties, and they can be used as binders for fillers such as insulating glass and foundry sand.

8 Claims, No Drawings

BETA-HYDROXYALKYLCARBAMYL-METHYLATED AMINOTRIAZINES

This is a division of application, Ser. No. 06/864,626, filed May 16, 1986, now U.S. Pat. No. 4,708,984.

The present invention relates to curable compounds and compositions and to methods of making and using them. More particularly, the present invention relates to novel beta-hydroxyalkylcarbamylmethylaminotriazine compounds and to curable compositions comprising the novel beta-hydroxyalkylcarbamylmethylaminotriazine, optionally, an active hydrogen-containing material or an amino resin, and, optionally, a cure catalyst. Coatings cured from the compositions have exceptional resistance to detergent and salt spray exposure and improved solvent resistance, making them well adapted for use in powder coatings, coil coatings and can coatings. The curable compositions also act as efficient binders for fillers, such as glass and foundry sand.

BACKGROUND OF THE INVENTION

Curable compositions containing aminotriazine compounds are known in the art. As is shown in Koral et al., U.S. Pat. No. 3,661,819, for example, a preferred family of aminotriazine curing agents comprises (i) a triaminotriazine compound of the formula:

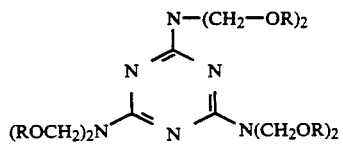

which will be depicted hereinafter as $C_3N_6(CH_2OR)_6$; or (ii) a benzoguanamine compound of the formula:

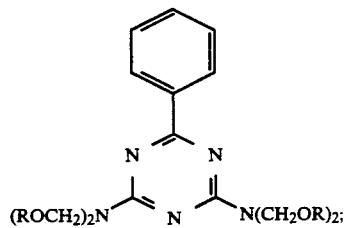

which will be depicted hereinafter as $C_3N_5(C_6H_5)(CH_2OR)_4$ wherein R is hydrogen or alkyl of from 1 to 12 carbon atoms. It is also known to use oligomers of such compounds, which are low molecular weight condensation products containing for example two, three or four triazine rings, joined by —CH$_2$OCH$_2$— linkages, as well as mixtures of any of the foregoing. These are used to self-condense or used to cure active hydrogen-containing materials, especially polymers which contain carboxyl groups, alcoholic hydroxy groups, amide groups and groups convertible to such groups, such as methylol groups, as well as amino resins, such as hydroxymethylated melamine, urea, benzoguanamine, phenol and oligomers thereof, as well as methylated, ethylated and butylated ethers thereof. When such curable compositions are applied to substrates as coatings or used as binders for glass fibers or for foundry sand, and then cured, excellent properties in terms of hardness, solvent resistance, tensile strength, etc., are imparted to the articles.

It has now been discovered that if aminotriazines of general formulae (i) and (ii) are reacted with betahydroxyalkyl urethanes, derivatives are formed which are also reactive to self-condense and to crosslink amino resins and/or active hydrogen-containing polymers, but the new coatings which are formed have much improved properties, e.g., detergent, salt spray, adhesion, color retention and especially abrasion resistance and hardness over those of the prior art. When used as binders, e.g., for glass or for fine sand, shaped articles are produced which have high tensile strengths and less tendency to emit formaldehyde in use, making them highly suitable for use as insulation and as foundry core molds.

Although it is known, e.g., from Valko, U.S. Pat. No. 4,435,559, to use beta-hydroxy urethanes as cross linkers for active hydrogen containing compounds, none of these prior art compounds are aminotriazine derivatives, and no property enhancement appears to have been achieved--merely lower curing temperatures.

It is also known to produce hydroxy-functional melamine derivatives by, for example, reaction of melamine with propanolamine, e.g., hydroxypropyl-functional melamine. Hydroxy alkyl carbamate functional melamine derivatives can also be made by reacting cyanuric chloride with the adduct of diethylenetriamine and propylene carbonate.

It has also now been discovered that the reaction of hydroxyalkyl carbamates with alkoxymethyl or hydroxymethyl melamines and benzoguanamines is very easily accomplished. The reaction products formed are unexpected, in that the amino group of the beta-hydroxyalkyl carbamate reacts exclusively with the alkylol ether groups of the aminotriazine to give a blocked isocyanate having terminal hydroxyl groups. Of great interest, no crosslinked product is formed in this preparation. Such an economical synthesis provides the novel multifunctional compounds of this invention, containing wide ranging yet predictable amounts of urethane linkages, reactive hydroxyl groups, and blocked isocyanate moieties for further elaboration.

In addition to their functions, mentioned above, in self-condensation or co-condensation to provide solvent-resistant, unusually hard coatings, further utility is found in reaction injection molding, e.g., with polyisocyanates, and the like.

SUMMARY OF THE INVENTION

According to the present invention there are provided triazine compounds selected from
(i) a triaminotriazine compound of the formula

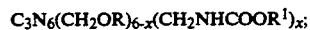

(ii) a benzoguanamine compound of the formula

(iii) an oligomer of (i) or of (ii) ; or
(iv) a mixture of at least two of any of (i), (ii) and (iii), wherein the R groups are, independently, hydrogen or alkyl of from 1 to 12 carbon atoms, the $R^1$ groups are, independently, beta-hydroxyalkyl of from 2 to 18 carbon atoms, alone, or combined with alkyl of from 1 to 18 carbon atoms, x is in the range of from about 3 to about 6, and y is in the range of from about 2 to about 4.

In preferred embodiments of the invention, x is in the range of from about 5 to about 6 and y is in the range of from about 3 to about 4. With respect to compound (i) R is preferably methyl and $R^1$ is beta-hydroxyethyl, beta-hydroxy propyl, e.g., a mixture of beta-hydroxy-alpha-methyl-ethyl and beta-hydroxy-beta-methylethyl, or a mixture of beta-hydroxypropyl and n-octyl. Also preferred are oligomers of (iii)(i) in which R is methyl and $R^1$ is beta-hydroxyethyl or beta-hydroxypropyl, as well as benzoguanamines (ii) wherein R is methyl and $R^1$ is beta-hydroxyethyl or beta-hydroxypropyl.

Also contemplated by the present invention are curable compositions comprising (a) a triazine compound selected from
  (i) a triaminotriazine compound of the formula $C_3N_6(CH_2OR)_{6-x}(CH_2NHCOOR^1)_x$;
  (ii) a benzoguanamine compound of the formula $C_3N_5(C_6H_5)(CH_2OR)_{4-y}(CH_2NHCOOR^1)_y$
  (iii) an oligomer of (i) or of (ii) ; or
  (iv) a mixture of at least two of any of (i), (ii) and (iii), wherein the R groups are, independently, hydrogen or alkyl of from 1 to 12 carbon atoms, the $R^1$ groups are, independently, beta-hydroxy-alkyl of from 2 to 18 carbon atoms, alone, or combined with alkyl of from 1 to 18 carbon atoms, x is in the range of from about 2 to about 6, and y is in the range of from about 2 to about 4; and, optionally, (b) an amino resin or an active hydrogen-containing material; and, optionally, (c) a cure catalyst.

In preferred features of this aspect of the invention, the material (b) is an amino resin containing hydroxymethyl or methoxymethyl groups, and preferably comprises a methylolmelamine or a methoxymethylolmelamine, and the polymeric material contains at least two reactive carboxyl, alcoholic hydroxy or amide groups, or a mixture of such groups, preferably a hydroxy-functional acrylic resin or a low molecular weight polyester polyol. Preferably the triazine will be as set forth specifically above, and the cure catalyst, if used, will be an acid, preferably p-toluenesulfonic acid, although it should be understood that many amino resins contain enough catalyst, e.g., residual acid catalyst, to make it unnecessary to add a cure catalyst separately. Other catalysts suitable for this purpose are quaternary ammonium hydroxides and organotin compounds.

Alternatively, the beta-hydroxy alkylcarbamylmethyl triazines can be used as a self-crosslinkable material in providing protective and/or decorative coatings and binders.

Also provided by the invention are articles of manufacture comprising substrates protectively coated with a baked and cured composition as defined above and articles of manufacture comprising fillers and/or reinforcements, such as glass, mineral fillers, sand, especially foundry mold sand which has been treated with the curable composition defined above, and then consolidated under heat into any desired shape.

DETAILED DESCRIPTION OF THE INVENTION

As starting materials to produce the beta-hydroxy alkylcarbamylmethylated triazines of this invention, there can be used the hydroxymethyl or alkoxymethyl melamines and/or benzoguanamines and oligmers thereof known in the art. Many of the starting materials are commercially available, and can be made by well known procedures. In accordance with the present invention, the starting materials are reacted with beta-hydroxy alkyl carbamates, such as beta-hydroxypropyl carbamate, alone, or in admixture with alkyl carbamates in the presence of an acid catalyst.

The beta-hydroxyalkyl carbamates are made, for example, by reacting a cyclic propylene carbonate with ammonia:

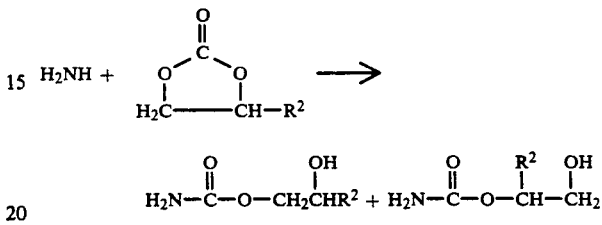

wherein $R^2$ is hydrogen, alkyl of from about 1 to about 16 carbon atoms. Depending on the manner in which the ring is opened, $R^2$ will be alpha- or beta-oriented with respect to the carbamyl function. The cyclic carbonates are made in known ways from the corresponding known 1,2-diols, which are illustrated, for example, in the Valko patent, and include, for example, 1,2-polyols ranging in molecular weight from about 62 to 286, typically ethylene glycol, 1,2-propylene glycol, 1,2-butanediol, 1,2-hexanediol, and the like, up to 1,2-octadecanediol.

An idealized reaction equation for the preparation of the new compounds from an alkoxymethylmelamine or a hydroxymethylmelamine is as follows:

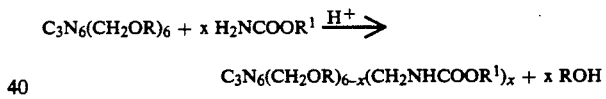

wherein R, $R^1$ and x are as defined above.

The mole ratio of beta-hydroxyalkyl carbamate is selected to provide the desired degree of substitution. By way of illustration, from 3 to 6 moles can be used. If less than 3 moles are used, per mole of melamine compound, premature gelation can be a problem. Reaction is typically carried out by heating in the melt or in solution, e.g., in benzene, toluene, xylene, chlorobenzene, dichlorobenzene, e.g., in the presence of catalytic amounts of acid, e.g., para-toluene sulfonic acid, at temperatures between 70° and 150° C., preferably 75°–120° C. Measurement of the quantity of alcohol (ROH) evolved gives an indication of reaction completion. With 6 moles of beta-hydroxy alkyl carbamate, reaction is usually not 100% complete, unless forced, but a high degree of substitution, x=5–6, is obtained. Analysis by gel permeation chromotography shows that treatment of hexamethoxymethylolmelamine with substantially less than 6 moles of beta-hydroxy alkyl carbamate gives a product which contains a similar oligomeric distribution as the triamino-triazine reactant comprised of a mixture of compounds with degrees of substitution ranging up to 6. Of course, only those compounds wherein two carbamylmethyl groups are present are crosslinkers according to this invention, even though residual alkoxymethyl groups can provide crosslinking.

Instead of alkoxymethylmelamines, hydroxymethylmelamines, and the corresponding benzoguanamine analogs and oligomers can be used as starting materials. With benzoguanamines, it is believed that if less than 2 moles of hydroxyalkyl carbamate is used per mole of triazine, premature gelation may be encountered. The products can be recovered by any convenient means after removal of byproduct water or alcohol is complete. Simply cooling them to room temperature will leave the product as a residue, and the acid catalyst can be removed by neutralization.

The substituents defined by R and $R^1$ in the formulae above can vary widely in carbon content, and the groups can be straight chain, branched chain and alicyclic. Representative compounds will be exemplified hereinafter.

The active hydrogen-containing materials have as the active hydrogen group a group selected from carboxyl, alcoholic hydroxyl, amido, primary amine, secondary amine (including imine), thiol and the like. The active hydrogen-containing materials useful herein are typically film-forming compositions. Illustrative examples of active hydrogen-containing materials are shown in the above-mentioned Koral patent, German Published Patent Application OLS 2,055,693, and in the above-mentioned Valko Patent. Typical polymers are acrylic polymers, polyesters, epoxy resins, and the like, providing that they contain active hydrogen groups.

Especially suitable are polyesters and polyacrylates containing pendant hydroxyl groups as reaction sites. The former are obtained in a known manner by the reaction of polycarboxylic acids with excess quantities of polyhydric alcohols; the latter are obtained by the copolymerization of acrylic or methacrylic acid derivatives with hydroxyl-group-containing derivatives of these acids, such as, for example, the hydroxyalkyl esters, optionally with the simultaneous use of additional vinyl compounds, such as, for example, styrene, or by the polymerization of caprolactone. Hydroxyl-group-containing polyurethanes can be obtained in known manner by the reaction of polyisocyanates with excess quantities of compounds containing at least two hydroxy groups. Suitable commercially available hydroxy-group-containing polyesters are CYPLEX® 1473 and CYPLEX® 1531 from American Cyanamid Company and Cargil Polyester 5776, and from Union Carbide Corp. under the trademark TONE® 0200. Suitable hydroxy-functional acrylic resins are available commercially from S. C. Johnson & Son, Inc. under the trademark JONCRYL® -500, and Rohm & Haas Co., under the trademark AT-400. Also suitable for use are the copolymer of 50% styrene, 20% hydroxypropyl methacrylate and 30% butyl acrylate of Example 5 of the above-mentioned German OLS 2,055,693 and the polyester of phthalic acid, adipic acid, ethanediol, and trimethylolpropane, with a hydroxy number of 130 and an acid number of 1.5 of Example 6 of the said OLS publication.

As set forth herein, the curable composition includes a cure catalyst; when appropriate--amino resins can cure with heat alone, because they usually contain residual acid catalyst. Typically, the cure catalyst is an acid which is soluble in the composition, such as a mineral acid, e.g., hydrochloric or nitric acids or an organic acid, such as p-toluenesulfonic acid or a naphthalene sulfonic acid, all of which are well known to those skilled in this art. The cure catalyst is used in amounts effective to accelerate cure at the temperatures employed, e.g., 120°–220° C. For example, the catalyst is used in amounts from about 0.1 to about 2.0 preferably 0.2 to 1% by weight based on the weight of the curable compositions. Quaternary ammonium hydroxides have also been used as catalysts in the same concentration range.

In the practice of the invention, the curable compositions can be adapted for use in solvent-based or water-based coating or binder compositions. Coating compositions comprising aqueous dispersions are particularly suited to application by electrodeposition. Generally the compositions will contain about 1 to 75 percent by weight of resin and novel aminotriazine combined, and the weight ratio of novel aminotriazine to resin will range from about 5 to about 40 parts to correspondingly from 60 to 95 parts of said resin.

In many instances a pigment composition and various conventional additives such as antioxidants, surface active agents, coupling agents, flow control additives, and the like, can be included. The pigment composition may be of any conventional type, such as, one or more pigments such as iron oxides, lead oxides, strontium chromate, carbon black, titanium dioxide, talc, barium sulfate, cadmium yellow, cadmium red, chromic yellow, or the like.

After deposition on a substrate, such as a steel panel, the coating composition is devolatilized and cured at elevated temperatures by any convenient method such as in baking ovens or with banks of infrared heat lamps. Curing can be obtained at temperatures in the range of from 120° C. to about 300° C., preferably from 150° C. to about 200° C. for from about 30 minutes at the lower temperatures to about 1 minute at the higher temperatures.

Alternatively, the new aminotriazines can be added to varnishes comprising, for example, amino resins, such as methylolated ureas, and melamines and used to impregnate surface sheets for laminates consolidating under heat and pressure using conventional conditions to produce laminates. They can also be formulated with normally thermoplastic hydroxyl group-containing polyurethanes and injection molded during which they react and cure in the mold to RIM (reaction-injection-molded) articles of manufacture.

By entirely conventional methods, the new compounds can be used in binder compositions for fillers and/or reinforcements ordinarily used with amino resins, such as cellulose, wood or paper flour or fibers, minerals such as talc, asbestos, wollastonite, silica, metals, such as silver, nickel, or non metals, such as carbon, and glass powder or fibers, textiles and sand, such as foundry sand.

DESCRIPTION OF THE PREFERRED EMBODIMENTS

The following examples illustrate the compounds and compositions of the present invention. They are not to be construed as limiting the claims in any manner. All parts are by weight.

EXAMPLE 1

Reaction Product of 6 Moles of Hydroxypropyl Carbamate With 1 Mole of Hexamethoxymethylmelamine Hexamethoxymethylmelamine (81.9g, 0.21 mole, American Cyanamid Co. CYMEL® 300), hydroxypropyl carbamate (150.0 g, 1.26 mole), and para-toluenesulfonic (1.16 g) are stirred at 75° C. in a flask equipped with a vacuum distillation head. During 80 minutes, the pressure is lowered in stages to 50 mm Hg and 37.2 g of methanol (1.02 mole, 81% of theoretical) is collected in the distillate receiver. The product in the reaction flask is cooled to near room temperature, where it is a clear, colorless, glass which is soluble in methanol, ethylene glycol or water. The product is of the formula:

$C_3N_6(CH_2NHCOOC_3H_6OH)_6$

EXAMPLES 2-5

If the general procedure of Example 1 is repeated, substituting analogs of beta-hydroxypropylcarbamate, the following beta-hydroxyalkylcarbamylmethyl melamines will be obtained:

| Example | $C_3N_6(CH_2NHCOOR^1)_{3-6}$ $R^1$ | |
|---|---|---|
| 2 | —CH$_2$CH$_2$OH | — |
| 3 | —CH$_2$CHOH<br>\|<br>CH$_2$CH$_3$ | + —CH—CH$_2$OH<br>\|<br>CH$_2$CH$_3$ |
| 4 | —CH$_2$CHOH<br>\|<br>CH$_2$(CH$_2$)$_4$CH$_3$ | + —CH—CH$_2$OH<br>\|<br>CH$_2$(CH$_2$)$_4$CH$_3$ |
| 5 | —CH$_2$CHOH<br>\|<br>CH$_2$(CH$_2$)$_{14}$CH$_3$ | + —CH—CH$_2$OH<br>\|<br>CH$_2$(CH$_2$)$_{14}$CH$_3$ |

EXAMPLE 6

Reaction Product of 5.25 Moles of Hydroxyethyl Carbamate With 1 Mole of Hexamethoxymethylmelamine Oligomer A mixture of 221.45 g, 0.607 mole of oligomeric methlolmethylated melamine (CYMEL ® 303, American Cyanamid Co.), 334.45 g, 3.1852 moles of beta-hydroxyethyl carbamate and 0.99 g of conc. nitric acid is heated at 100° C. under a constant nitrogen flow. Vacuum is then applied to maintain a constant distillation of methanol. The maximum vacuum applied is 50 mm Hg. The reaction is stopped after 50 minutes.

The product is recovered by dissolving the reaction mixture in water containing one equivalent of base to neutralize the acid catalyst and to provide a solution containing 45% solids, by weight. The product is of the formula:

$C_3N_6(CH_2NHCOOCH_2CH_2OH)_{5.25}$
$(CH_2OCH_3)_{0.75}$

EXAMPLE 7

Reaction Product of 2 Moles of n-Octyl Carbamate and 4 Moles of Hydroxy-Propyl Carbamate With 1 Mole of Hexamethoxymethyl Melamine Hexamethoxymethyl melamine (13.5 g, 0.0346 mole) and 12.0 g (0.0694 mole) of n-octyl carbamate are stirred at 75° C. in a flask equipped with a vacuum distillation head and a receiver cooled in dry ice-acetone. Then 0.18 g (0.0010 mole) of p-toluenesulfonic acid is added. During 50 min., the pressure is lowered in stages to 50 mm. Hg and 2.36 g of methanol (0.0738 mole, 106% of theoretical) is collected in the receiver. Gas chromatography of the reaction mixture shows complete consumption of the n-octyl carbamate.

Then 16.5 g (0.139 mole) of hydroxypropyl carbamate is added. During 70 min., the pressure is lowered in stages to 50 mm Hg and 3.86 g of methanol (0.121 mole, 87% of theoretical) is collected in the receiver.

After cooling to room temperature, the reaction product is a colorless near-solid. It is dissolved in 150 ml of methylene chloride by stirring for 45 min. at room temperature. The solution is washed in a separatory funnel with two 50 ml portions of 5% Na$_2$CO$_3$ solution, and dried over anhydrous granular K$_2$CO$_3$. Rotary vacuum evaporation affords 44.2 g (96% theoretical yield) of a moderately viscous liquid which is easily dissolved at 75% solids concentration in methyl isobutyl ketone to give a colorless, mobile solution. The product is of the formula:

$C_3N_6(NHCOOC_8H_{17})_2 (CH_2NHCOOC_3H_8OH)_4$

EXAMPLE 8

If the general procedure of Example 1 is repeated, substituting an oligomeric methylolated melamine methyl ether (American Cyanamid Co., CYMEL ® 303), the corresponding beta-hydroxy propylcarbamyl-methylated oligomeric melamine of this invention will be obtained.

EXAMPLE 9

If the general procedure of Example 1 is repeated, substituting a tetramethoxymethylolbenzoguanamine (American Cyanamid Co., CYMEL ® 1123), the corresponding beta-hydroxy-propylcarbamylmethylated benzoguanamine of this invention will be obtained.

In the following examples, the beta-hydroxy alkyl-carbamylmethylated triazines of this invention are formulated into curable compositions and evaluated as coatings.

Procedure for Coatings Preparation

The hexa(hydroxypropylcarbamylmethyl) melamine is used as a 75% solution in methanol and the tetra(hydroxypropylcarbamylmethyl)di(n-octyl-carbamyl-methyl) melamine is used as a 65% solution in methyl isobutyl ketone. The polymeric components are supplied as 60% to 100% solids.

The formulated coatings are made up at 55-65% solids by dilution to appropriate viscosity with solvents such as n-butanol or MIBK.

The coatings are drawn down on 4"×12"×12 ga. BONDERITE ® 100-treated steel panels (from Parker Chemical Co.) by using a wire-wound applicator (WIRE-CATOR ®). In some cases FC-431 (3M Co.), a fluorochemical surfactant, is added to the formulation to improve flow-out. After standing for a few minutes at room temperature to improve leveling, the panels are placed horizontally in a pre-heated forced-draft air oven for curing at the appropriate time and temperature. Solvent resistance is used as the screen for curing completeness. The 70° C. Detergent Reistence is measured by ASTM D714, rated on a scale of 1-10; 10 means no blistering. Salt Spray Resistance is by ASTM D1654. Taber Abrasion is measured by ASTM D4060. Forward and Reverse Impact Strength is measured by ASTM D-3281.

EXAMPLES 10–13

The crosslinker of Example 1 herein, the reaction product of 6 moles of beta-hydroxypropyl carbamate and 1 mole of hexamethoxymethyl melamine is used with a methoxymethyl melamine oligomer and p-toluenesulfonic acid as cure catalyst. The formulations used and the properties of the cured films are set forth in Table 1:

TABLE 1

Hydroxyalkylcarbamyl Methyl Melamine Cured With Melamine Resin

| Example | 10 | 11 | 12 | 13 |
|---|---|---|---|---|
| Composition (parts by weight) | | | | |
| 6-beta HOPC[a] | 70 | 70 | 50 | 30 |
| Melamine Resin[b] | 30 | 30 | 50 | 70 |
| p-TSA[c] | 1 | 1 | 1 | 1 |
| Cure Temp., °C. | 125 | 150 | 125 | 125 |
| Cure Time, min. | 30 | 20 | 130 | 130 |
| Properties | | | | |
| MEK Resistance[d] | P | P | P | P |
| Methanol Resistance | P | P | P | P |
| Knoop Hardness | 57 | 40 | 25 | 25 |
| Reverse Impact, in. lbs. | 5 | — | 5 | 5 |

[a]beta-hydroxypropylcarbamylmethyl melamine (Example 1);
[b]CYMEL ® 303, American Cyanamid Co.;
[c]p-Toluenesulfonic acid; and
[d]P = Passes 200 double rubs.

EXAMPLES 14–19

The reaction products of Example 1 and 7 herein, are used with a hexamethoxymethyl melamine oligomer resin and a reaction product of 2 moles of n-octyl carbamate and 1 mole of hexamethoxymethyl melamine using p-toluenesulfonic acid as cure catalyst. An epoxy resin, a glycidyl ether of bisphenol-A, EPON ® 1001, Shell Chemical Co., is included in some of the formulations. The formulations used and the properties of the cured coatings are set forth in Table 2:

TABLE 2

Hydroxyalkylcarbamyl-methylated Melamine Cured Resin Coatings

| Example | 14 | 15 | 16 | 17 | 18 | 19 |
|---|---|---|---|---|---|---|
| Composition (parts by weight) | | | | | | |
| Hexa(hydroxypropylcarbamylmethyl) melamine | 40 | 30 | 30 | — | — | — |
| Tetra(hydroxypropylcarbamylmethyl)di(n-octylcarbamylmethyl) melamine | — | — | — | 60 | 50 | 33 |
| Hexa(methoxymethyl) melamine | — | — | — | 40 | 50 | 67 |
| Tetra(methoxymethyl)di(n-octyl-carbamylmethyl) melamine | 40 | 35 | 30 | — | — | — |
| EPON ® 1001, epoxy resin | 20 | 35 | 40 | — | — | — |
| p-Toluenesulfonic Acid | 1 | 1 | 1 | 0.5 | 0.5 | 0.5 |
| FC-431(fluorochemical surfactant) | — | — | — | 0.1 | 0.1 | 0.1 |
| Cure, °C./min. | 150/20 | 150/20 | 150/20 | 125/20 | 125/20 | 125/20 |
| Properties | | | | | | |
| MEK Resistance | P | P | P | P | P | P |
| Knoop Hardness | 12 | 15 | 17 | 16 | 16 | 16 |
| Reverse Impact, in. lbs. | 5 | 5 | 5 | 5 | 5 | 5 |
| Forward Impact, in lbs. | 15 | 15 | 15 | 15 | 15 | 15 |
| 70° C. Detergent, hrs./blist. rating | — | — | — | 40/10 | 40/10 | 40/10 |

Excellent coatings are obtained in accordance with this invention.

EXAMPLES 20–25

The reaction products of Examples 1 and 7 herein are used with a hexamethoxymethyl melamine oligomer resin to crosslink several commercially available hydroxy functional polymers. An epoxy resin, EPON ® 1001 is included in some of the formulations. The formulations used and the properties of the cured coatings are set forth in Table 3, as follows:

TABLE 2

Hydroxyalkylcarbamyl-methylated Melamine Crosslinked Acrylic and Caprolactone Resins

| Example | 20 | 21 | 22 | 23 | 24 | 25 |
|---|---|---|---|---|---|---|
| Composition (parts by weight) | | | | | | |
| Hexa(hydroxypropylcarbamylmethyl) melamine | 15 | 10 | 35 | 20 | — | — |
| Tetra(hydroxypropylcarbamylmethyl)di(n-octylcarbamylmethyl)melamine | — | — | — | — | 31 | 33 |
| Hexa(methoxymethyl)melamine[a] | 15 | 10 | 25 | 25 | 33 | 42 |
| AT-400(hydroxyfunctional) polyacrylate[b] | 70 | 80 | — | — | — | — |
| JONCRYL ® 400 (hydroxyfunctional) polyacrylate[c] | — | — | 40 | 55 | — | — |
| TONE ® 0200 (polycaprolactone diol)[d] | — | — | — | — | — | 15 |
| EPON ® 1001, epoxy resin[e] | — | — | — | — | 14 | 10 |
| p-Toluenesulfonic Acid | 1 | 1 | 0.5 | 0.5 | 0.5 | 0.5 |
| FC-431(fluorochemical surfactant) | — | — | 0.1 | 0.1 | 0.1 | 0.1 |
| Cure, °C. | 125 | 125 | 125 | 125 | 125 | 125 |
| Cure Time, min. | 20 | 20 | 20 | 20 | 20 | 20 |

TABLE 3

| Example | 20 | 21 | 22 | 23 | 24 | 25 |
|---|---|---|---|---|---|---|
| Properties | | | | | | |
| MEK Resistance | P | P | P | P | P | P |
| Knoop Hardness | 13 | 9.3 | 18 | 15 | 14 | 12 |
| Reverse Impact, in. lbs. | 10 | 10 | 5 | 5 | 5–10 | 15 |
| Direct Impact, in. lbs. | — | — | 20–30 | 20–30 | 30 | 50 |
| 70° C. Detergent, hrs./Blister Rating | — | — | 24/rust | 24/D6 | 96/10 | 96/M8 |
| Salt Spray, Hrs./ | — | — | 96/2 | 96/7 | — | — |

TABLE 3-continued

| Example | 20 | 21 | 22 | 23 | 24 | 25 |
|---|---|---|---|---|---|---|
| Creepage (mm) Taber Abrasion, mg lost/cycle × 1000 | — | — | 45 | 47 | 67 | 17 |

[a] American Cyanamid Co.
[b] Rohm & Haas & Co.
[c] S. C. Johnson & Sons, Inc.
[d] Union Carbide Corp.
[e] Shell Chemical Co.
[f] 3M Co.

Excellent coatings are obtained in accordance with this invention.

A review of the data in the foregoing tables indicates that excellent properties are obtained with the beta-hydroxy alkylcarbamylmethylated triazines of this invention.

It is generally the case also, that the betahydroxyalkylcarbamylmethylated melamines of this invention afford coatings with good color stability. Finally, the data show that while outstanding resistance properties and color stability have been obtained with the betahydroxyalkylcarbamate melamines, other important and desirable coatings properties such as Knoop hardness, impact and solvent resistance (MEK rubs +200) have been maintained as is the case with conventional resins.

The hydroxyalkylcarbamylmethylated-melamines and -benzoguanamines of this invention are useful as binders for fillers and/or reinforcements, e.g., mineral and glass fillers as is illustrated by the following examples.

EXAMPLE 26-27

A binder formulation for fiberglass insulation is prepared and screened in a standard test by binding very fine glass beads in a dogbone shaped bonded test piece. The tensile strength of the test piece is then determined by a standard method.

The binder formulation comprises:
1.33 parts by weight of a 75 wt. % solution of 6-HOPC (the product of Example 1);
8.00 parts of 25 wt. % aqueous low molecular weight starch (RAISIO ® K-55);
0.60 parts additional water; and
0.60 parts of 10% phosphoric acid in water.

The mixture is thoroughly blended with 60 parts by weight of fine glass shot and pressed into two dogbone shaped molds. The pieces are removed from the mold and cured in an oven at 140° C. for 60 minutes. The cured coatings (¼×1" cross section at neck) are found to have tensile strengths of 80 and 110 lbs. (320 and 440 psi) compared to 0 psi with no binder and 10-30 psi for poor binder formulations.

If foundry sand is substituted for glass and coated with the hydroxypropyl carbamylmethylated melamine of this invention, starch and acid, the coated sand will cure into foundry molds eminently suitable for metal casting (little or no formaldehyde odor is detectable upon exposure to foundry temperatures).

The above-mentioned patents and publications are incorporated herein by reference. Many variations of this invention will suggest themselves to those skilled in this art in light of the above, detailed description. For example, instead of reacting hexamethoxymethylmelamine or an oligomer with beta-hydroxypropylcarbamate, tetramethoxymethylbenzoguanamine can be reacted with beta-hydroxypropylcarbamate to obtain a crosslinker according to this invention. Instead of using beta-hydroxypropylcarbamylmethylated melamine as curing agents in the formulations of Tables 1-3, the corresponding beta-hydroxy alkyl carbamylmethylated melamine and melamine oligomers of Examples 2-6 can be used. Instead of p-toluenesulfonic acid as cure catalyst, mineral acids, such as hydrochloric acid and nitric acid can be used. Instead of hydroxyfunctional polyesters and polyacrylates, epoxy resins, such as the polyglycidylethers of bisphenol A and the reaction products thereof with amines and ammonia can be used. All such obvious modifications are within the full intended scope of the appended claims.

We claim:

1. A triazine compound selected from
   (i) a triaminotriazine compound of the formula

   $C_3N_6(CH_2OR)_{6-x}(CH_2NHCOOR^1)_x$, or;

(ii) a benzoguanamine compound of the formula

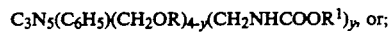
   $C_3N_5(C_6H_5)(CH_2OR)_{4-y}(CH_2NHCOOR^1)_y$, or;

(iii) an oligomer of (i) or (ii),
   wherein the R groups are, independently, hydrogen or alkyl of from 1 to 12 carbon atoms, the $R^1$ groups are, independently, beta-hydroxyalkyl of from 2 to 18 carbon atoms or alkyl of from 1 to 18 carbon atoms, wherein at least one $R^1$ is beta-hydroxyalkyl, and x is in the range of from about 3 to about 6, any y is in the range of from about 2 to about 4.

2. A triaminotriazine compound (i) as defined in claim 1 wherein x is in the range of from about 5 to about 6.

3. A triaminotriazine compound (i) as defined in claim 1 wherein $R^1$ comprises a mixture of beta-hydroxy-alpha-methylethyl and beta-hydroxy-beta-methylethyl.

4. A benzoguanamine compound (ii) as defined in claim 1 wherein R is methyl and $R^1$ is beta-hydroxyethyl or beta-hydroxypropyl.

5. A triaminotriazine compound (i) as defined in claim 1 wherein one or more of the $R^1$ moieties are selected from the group consisting of:
   (a) beta-hydroxyethyl,
   (b) beta-hydroxypropyl, and
   (c) a mixture of beta-hydroxyethyl and beta-hydroxypropyl.

6. An oligomer of a triaminotriazine compound of the formula:

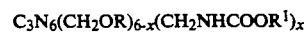
   $C_3N_6(CH_2OR)_{6-x}(CH_2NHCOOR^1)_x$ wherein the R groups are, independently, hydrogen or alkyl from 1 to 12 carbon atoms, the $R^1$ groups are, independently, hydrogen, alkyl of from 1 to 12 carbon atoms, the $R^1$ groups are, independently, beta-hydroxyalkyl of from 2 to 18 carbon atoms or alkyl of from 1 to 18 carbon atoms, wherein at least one $R^1$ is beta-hydroxyalkyl, and x is in the range of from about 3 to about 6.

7. An oligomer of a benzoguanamine compound of the formula:

   $C_3N_5(C_6H_5)(CH_2OR)_{4-y}(CH_2NHCOOR^1)_y$ wherein the R groups are, independently, hydrogen or alkyl from 1 to 12 carbon atoms, the $R^1$ groups are, independently, beta-hydroxyalkyl of from 2 to 18 carbon atoms or alkyl of from 1 to 18 carbon atoms, wherein at least one $R^1$ is beta-hydroxyalkyl, and y is in the range of from 2 to about 4.

8. The compound beta-hydroxypropylcarbamylmethylmelamine represented by the formula:

   $C_3N_6(CH_2NHCOOC_3H_6OH)_6$

* * * * *